United States Patent [19]

Kraft et al.

[11] 4,378,718
[45] Apr. 5, 1983

[54] HANDLE FOR PIVOTABLE MACHINE PARTS

[75] Inventors: Winfried Kraft, Werdorf; Artur Reichel, Wetzlar; Günter Holmok, Lahnau-Waldgirmes, all of Fed. Rep. of Germany

[73] Assignee: Ernst Leitz Wetzlar GmbH, Wetzlar, Fed. Rep. of Germany

[21] Appl. No.: 171,997

[22] Filed: Jul. 24, 1980

[30] Foreign Application Priority Data

Jul. 25, 1979 [DE] Fed. Rep. of Germany ... 7921193[U]

[51] Int. Cl.³ .............................................. G01N 1/06
[52] U.S. Cl. ....................................... 83/592; 83/170; 83/597; 83/642; 83/915.5
[58] Field of Search ................. 83/591, 592, 596, 597, 83/642, 915.5, 170, 70; 145/61 G–61 R

[56] References Cited

U.S. PATENT DOCUMENTS

| 108,141 | 10/1870 | Houseman et al. | 145/61 C X |
|---|---|---|---|
| 470,687 | 3/1892 | Koelzer | 145/61 G |
| 664,118 | 12/1900 | Becker | 83/915.5 X |
| 861,010 | 7/1907 | Zeman | 145/61 EA |
| 1,677,572 | 7/1928 | Walkley | 145/61 E |
| 2,056,054 | 9/1936 | Osgood | 145/61 C |
| 2,066,381 | 1/1937 | Albertson | 83/490 X |
| 3,220,290 | 11/1965 | Shandon | 83/915.5 X |

Primary Examiner—Donald R. Schran
Attorney, Agent, or Firm—Schwartz, Jeffery, Schwaab, Mack, Blumenthal & Koch

[57] ABSTRACT

Disclosed is a handle adapted for grasping by the hand of an operator for operating a pivotable machine part, comprising a thumb supporting member attached to the machine part for supporting the operator's thumb and a grip part connected to the machine part for gripping by the rest of the fingers of the operator's hand. Also disclosed is a microtome embodying this handle.

6 Claims, 4 Drawing Figures

HANDLE FOR PIVOTABLE MACHINE PARTS

BACKGROUND OF THE INVENTION

The present invention relates to a handle for pivotable machine parts, for example, the blade holder designed as a pivoting arm of a cryogenic microtome.

Known handles for pivotable machine parts in general comprise a pivoting arm connected with a frequently rotatable spherical knob, with the pivoting arm being fastened to the machine part to be operated. For this purpose, the knob is gripped by the hand of the operator and is then actuated. In the case of precision instruments, such as, for example, cryogenic microtomes, it is often necessary to repeatedly pivot the blade-holding pivoting arm for longer periods of time using the known knob as the actuating handle. In the process, the hand of the operator easily slips from the knob, so that its grip must be reestablished, which over longer periods of time is tiring and additionally may interfere with the continuous guidance of the cutting operation.

SUMMARY OF THE INVENTION

It is therefore an object of the present invention to provide an improved handle for actuating a pivotable machine part.

It is a particular object of the invention to provide an improved handle for the pivoting arm of a cryogenic microtome, whereby slipping of the hand operating the handle is reliably prevented even during extended operations and the gripping of the handle is facilitated.

It is also an object of the invention to provide an improved microtome embodying the handle according to the invention.

In order to accomplish the foregoing objects, there has been provided in accordance with the present invention a handle adapted for grasping by the hand of an operator for operating a pivotable machine part, comprising a thumb supporting member attached to the machine part for supporting the operator's thumb and a grip part connected to the machine part for gripping by the rest of the fingers of the operator's hand. In one embodiment, the thumb support member is mounted on the machine part and the thumb supporting member also carries the grip part, whereas in another embodiment, the grip part is mounted on the machine part and also carries the thumb support member.

In accordance with another aspect of the present invention, there has also been provided an improved microtome including the above-described handle.

Further objects, features and advantages of the present invention will become apparent from the description of preferred embodiments which follows, when considered together with the attached figures of drawing.

DETAILED DESCRIPTION OF PREFERRED EMBODIMENTS

Figure 1:
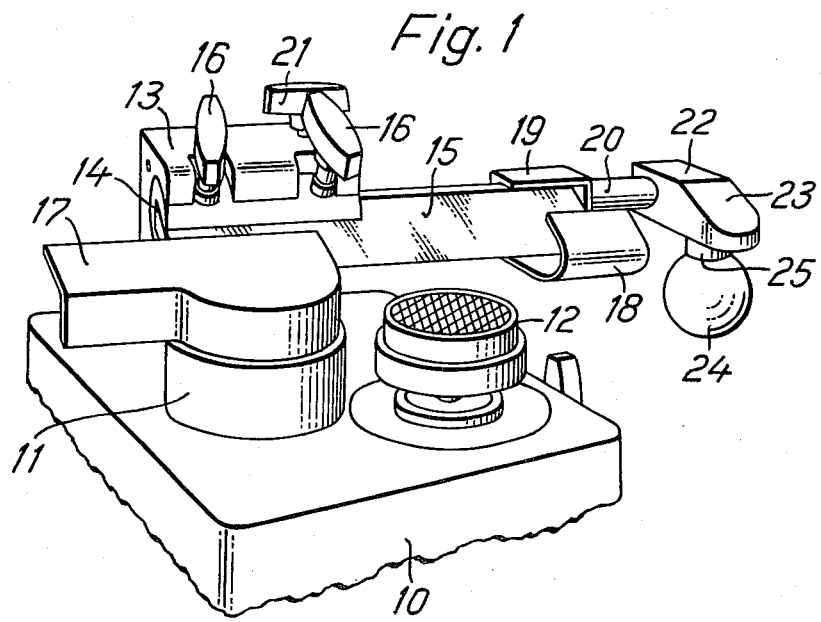
FIG. 1 is a perspective view of a cryogenic microtome with the handle according to the invention in the simplest possible form.

According to the invention, the handle is provided with a special thumb support for the thumb and a gripping part for the rest of the fingers of the operator.

A particularly simple and clearly arranged layout is obtained by securing the thumb support on the machine part and having it carry or support the grip part. Conversely, it may be convenient for numerous instruments to mount the grip part directly on the machine part and to arrange the thumb support on the grip part.

The thumb support may be provided with a recess for insertion of the tip of the thumb. However, the thumb support may also be equipped with a bearing surface for the application or insertion of the tip of the thumb, wherein the recess or bearing support, respectively, may be oval or round in shape, whereby it is adapted to the shape of the tip of the thumb. Further, the bearing surface may be mounted on the thumb support in an adjustable or swivelling manner. In this way, it is possible to equalize not only differences in the hand size of different users, but also friction between the tip of the thumb and the bearing surface may be eliminated. For adjusting, it is sufficient to provide a slit in the thumb support wherein the bearing surface may be displaced, and a set screw to immobilize it in the position desired.

The grip part may be designed in a manner known in itself, for example, as a pivoting knob, an elongated body or in an otherwise ergonomically adapted shape. It should be understood that a simple pin may also be provided as the grip part, which may be equipped with finger fluting in order to improve the grip.

In the drawing, several examples of the embodiment of the handle of the invention are demonstrated schematically, in connection with a cryogenic microtome.

The cryogenic microtome shown in FIG. 1 essentially consists of a stand 10, upon which a swivel bearing 11, a cryogenic table 12 and a blade holder 13 are arranged. In the blade holder 13, a blade clamp 14 is mounted for the blade 15, this clamp being adjustable by means of two set screws 16. In front of the blade, in the area of the left hand (in the plane of the drawing) terminal edge, a blade guard 17 is mounted on the swivel bearing 11, while the right hand terminal edge is surrounded by a cover 18. The latter is connected with a holder 19, which is arranged on a pivoting arm 20. The blade guard 17 and the cover 18 protect the edge of the blade 15 against damage and the operator against injury.

The pivoting arm 20 is removably clamped with one of its ends in the blade holder 13 by means of a retaining screw 21 while its free end carries an integrally shaped thumb support 22. The latter is essentially square in this case and has a bevel 23 for the support of the operator's thumb. On the bottom side of the thumb support 22, a grip part 24 is provided, which in the present case has the configuration of a sphere and is rotatably mounted, preferably on a cylindrical connecting piece 25.

Figure 1A:
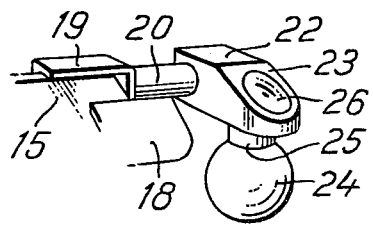
FIG. 1a is an isolated perspective view of a thumb support with a recess.

The thumb support 22 shown in FIG. 1a is equipped on its bevelled surface 23 with an oval recess 26, capable of receiving the tip of the thumb.

Figure 1B:
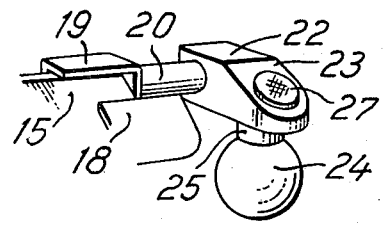
FIG. 1b is an isolated perspective view of a thumb support with a bearing surface.

In the embodiment shown in FIG. 1b, the thumb support is equipped with a circular, recessed overlay 27, which is capable of rotation around its center and is displaceable on the bevel 23 of the thumb support 22 in the longitudinal direction of the latter. On the bottom side of the thumb support 22, the cylindrical connecting piece 25 is integral with the thumb support and is surrounded by the spherical grip part 24, which is rotatable around the connecting piece 25. The grip 24 is held by the other fingers of the operator during actuation of the handle. The axis of the connecting piece 25, as readily seen, forms an angle of less than 90° with the surface of the overlay 27.

Figure 2:
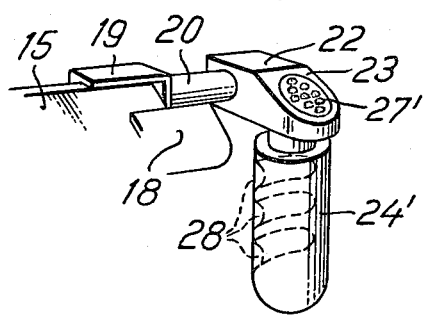
FIG. 2 is an isolated perspective view of a handle with a thumb support and a bearing surface having a gripping part in a special embodiment.

In the embodiment according to FIG. 2, the overlay 27' has an oval configuration and the grip part 24' has the form of an elongated handle, equipped with finger fluting 28 to provide a better grip (the fluting is indicated by the broken line). The grip part 24' is equipped with threading, not shown, so that its height may be adjusted with respect to the thumb support 22.

It is readily seen that, in the simplest case, the grip part may consist of a simple pin.

What is claimed is:

1. In a microtome having a blade holder in the form of an arcuately pivotable arm, a handle for said blade holder comprising a thumb support member for receiving the thumb of an operator, said thumb support member being essentially square and having a bevelled surface for supporting the operator's thumb, a grip member for receiving the remaining fingers of the hand of an operator, said grip member being rotatably mounted on the bottom side of said thumb support by a cylindrical connecting piece, the axis of said connecting piece forming an angle of less than 90° with the bevelled surface of said thumb support, and means for adjusting the relative position of said thumb support member and said grip member.

2. Apparatus according to claim 1, wherein said thumb support member is mounted on said pivotable arm and said grip member is carried on said thumb support member.

3. Apparatus according to claim 1 or 2, wherein said thumb support member is provided with an elongated recess for receiving the tip of the thumb.

4. Apparatus according to claim 1 or 2, wherein said grip member has the form of a sphere.

5. Apparatus according to claim 1 or 2, wherein said grip member has the form of an elongated body.

6. Apparatus according to claim 1 wherein said thumb support member is provided with an adjustably positionable, rotatable overlay.

* * * * *